(12) United States Patent
Von Schuckmann

(10) Patent No.: US 10,643,118 B2
(45) Date of Patent: May 5, 2020

(54) HANDHELD DEVICE WITH A COUNTER AND COUNTER

(71) Applicant: Alfred Von Schuckmann, Kevelaer (DE)

(72) Inventor: Alfred Von Schuckmann, Kevelaer (DE)

(*) Notice: Subject to any disclaimer, the term of this patent is extended or adjusted under 35 U.S.C. 154(b) by 187 days.

(21) Appl. No.: 15/534,286

(22) PCT Filed: Dec. 1, 2015

(86) PCT No.: PCT/EP2015/078170
§ 371 (c)(1),
(2) Date: Jun. 8, 2017

(87) PCT Pub. No.: WO2016/091652
PCT Pub. Date: Jun. 16, 2016

(65) Prior Publication Data
US 2017/0344874 A1  Nov. 30, 2017

(30) Foreign Application Priority Data
Dec. 10, 2014 (DE) .................. 10 2014 118 325

(51) Int. Cl.
*G06M 1/04* (2006.01)
*G06M 1/14* (2006.01)
(Continued)

(52) U.S. Cl.
CPC ........ *G06M 1/042* (2013.01); *A61M 15/0065* (2013.01); *G06M 1/143* (2013.01); *G06M 1/163* (2013.01)

(58) Field of Classification Search
CPC ............ A61M 15/009; A61M 15/0065; A61M 15/0066; A61M 15/0068; A61M 15/007;
(Continued)

(56) References Cited

U.S. PATENT DOCUMENTS

| | | |
|---|---|---|
| 5,349,945 A | 9/1994 | Wass et al. |
| 6,435,372 B1 | 8/2002 | Blacker et al. |
| 7,448,342 B2 | 11/2008 | Von Schuckmann |
| 8,132,565 B2 | 3/2012 | Von Schuckmann |

(Continued)

FOREIGN PATENT DOCUMENTS

| | | |
|---|---|---|
| WO | 92/09324 A1 | 6/1992 |
| WO | 99/36115 A2 | 7/1999 |

(Continued)

OTHER PUBLICATIONS

International Search Report of PCT/EP2015/078170, dated Apr. 18, 2016.

*Primary Examiner* — Kendra D Carter
*Assistant Examiner* — Elliot S Ruddie
(74) *Attorney, Agent, or Firm* — Collard & Roe, P.C.

(57) ABSTRACT

A counter for a handheld device for dispensing a pharmaceutical substance, has a housing, at least one counter wheel which has readable characters, and a drive part which is designed to rotate the counter wheel, the counter wheel being rotatably attached to a mounting part. The mounting part of the counter is designed independently of the housing, and the drive part is directly attached to the mounting part. The counter can have at least one counter wheel which has readable characters and a drive part which is designed to rotate the counter wheel. The counter wheel has readable characters and is designed in a cylindrical manner and with a central axis, and has a drive part which is designed to rotate the counter wheel, the counter wheel being provided with an engagement toothing via which the drive part acts on the counter wheel so as to rotate same, the drive part having a rotational axis.

18 Claims, 5 Drawing Sheets

(51) Int. Cl.
*G06M 1/16* (2006.01)
*A61M 15/00* (2006.01)

(58) Field of Classification Search
CPC .......... A61M 15/0071; A61M 15/0073; A61M 15/0075; A61M 15/0076; A61M 15/0078; A61M 15/0081; A61M 15/0091; A61M 15/008; A61M 15/0093; A61M 15/0095; A61M 15/0096; A61M 15/00; G06M 1/04; G06M 1/041; G06M 1/042; G06M 1/044; G06M 1/14; G06M 1/143; G06M 1/146; G06M 1/16; G06M 1/163; G06M 1/166
USPC .................... 235/1 B, 60 C, 103; 453/30, 58
See application file for complete search history.

(56) References Cited

U.S. PATENT DOCUMENTS

| | | |
|---|---|---|
| 8,459,253 B2 | 6/2013 | Howgill |
| 2004/0149772 A1* | 8/2004 | Ouyang .............. A61M 15/009 222/36 |
| 2010/0078490 A1* | 4/2010 | Fenlon ................ A61M 15/009 235/91 R |
| 2010/0229855 A1* | 9/2010 | Howgill .............. A61M 15/009 128/200.23 |
| 2015/0250959 A1* | 9/2015 | Stuart ................... G06M 1/041 128/200.23 |

FOREIGN PATENT DOCUMENTS

| | | |
|---|---|---|
| WO | 2006/051073 A1 | 5/2006 |
| WO | 2007/104694 A1 | 9/2007 |
| WO | 2008/121459 A1 | 10/2008 |

* cited by examiner

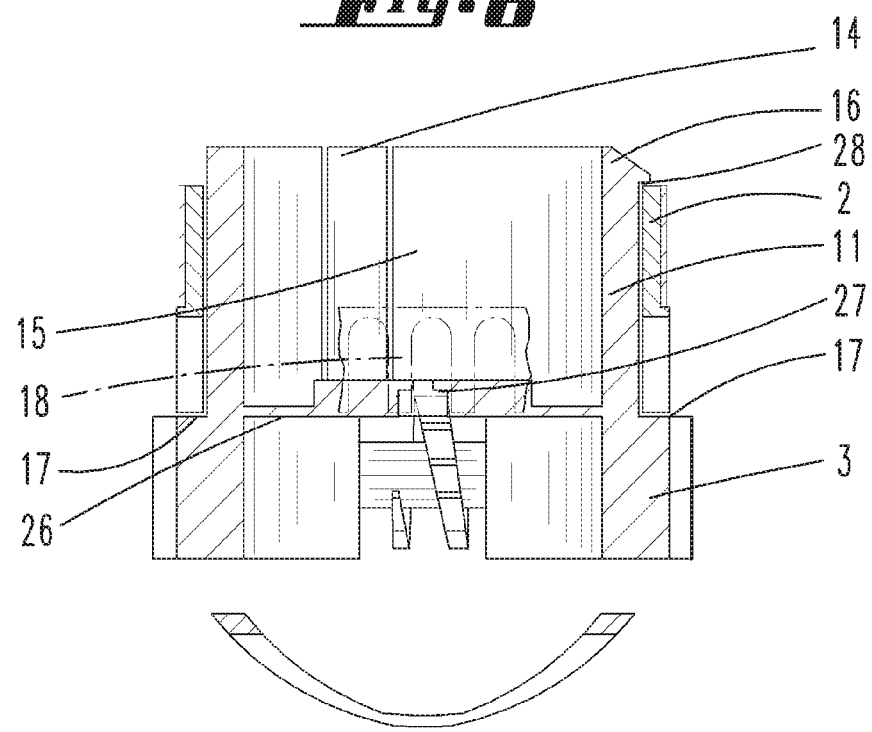
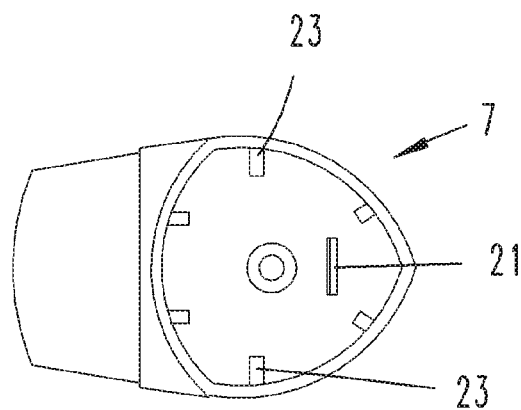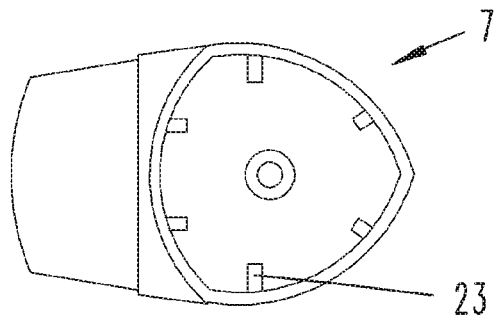

HANDHELD DEVICE WITH A COUNTER AND COUNTER

CROSS REFERENCE TO RELATED APPLICATIONS

This application is the National Stage of PCT/EP2015/078170 filed on Dec. 1, 2015, which claims priority under 35 U.S.C. § 119 of German Application No. 10 2014 118 325.8 filed on Dec. 10, 2014, the disclosures of which are incorporated by reference. The international application under PCT article 21(2) was not published in English.

The invention initially pertains to a handheld device for dispensing a pharmaceutical substance with a housing and a counter wheel according to the characteristics of the preamble of claim 11.

The invention furthermore pertains to a counter for a handheld device for dispensing a pharmaceutical substance according to the characteristics of the preamble of claim 12.

Such counters are already known in different variations. In this context, we particularly refer to WO 2007/104694 A1 (U.S. Pat. No. 8,132,565 B2).

This publication discloses a counter that is during the intended use arranged on the upper side of a reservoir chamber of the handheld device, wherein said reservoir chamber contains the pharmaceutical substance. It is acted upon due to a direct pressure actuation by the user. A rotational axis of the drive part is accommodated in two bearing formations that are integrally formed on the inner side of an actuating button such that they protrude downward. The counter wheel is accommodated between the actuating button and a housing wall, both of which respectively also form part of the housing.

With respect to the prior art, we furthermore refer to WO 2006/051073 A1 (U.S. Pat. No. 7,448,342 B2). The counter known from this publication is during the intended use positioned underneath a closed receptacle containing the pharmaceutical substance and arranged in the handheld device. It is actuated by pressing the receptacle downward. The counter wheel is accommodated between a lower ring part and an upper housing cover. The drive part is loosely inserted and—initially—acts upon the counter wheel by means of a disk part, as well as by means of a planet wheel. In the object of the initially cited publication, the only return spring provided is the return spring that altogether returns the actuating button and is accommodated between the actuating button and an intermediate bottom of the housing. In the object of the additionally cited publications, the drive part features springable driving fingers that act upon the disk part.

WO 2008/121459 A1 discloses a counter, in which the drive part is realized rotatably relative to the mounting part. The lower edge of the counter wheel is realized in the form of a closed peripheral edge. The return spring interacts with an intermediate wheel. It is arranged above the mounting part referred to an actuating direction.

WO 92/09324 A1 discloses a counter, in which the counter wheel features a toothing on its upper edge and the drive part is attached to the mounting part by means of a mounting. The counter as such cannot be reset by a return spring. The return spring, which only acts upon the driving element, is not used as a drive. The rotational axis of the drive part extends outside a part that is referred to as counter wheel.

WO 99/36115 A2 discloses a counter that is realized in a disk-shaped fashion. A separate toothing part is provided outside the peripheral edge of the counter wheel.

Based on the above-described prior art, the invention aims to disclose an advantageous handheld device with a housing and a counter, as well as an advantageously designed counter.

With respect to the handheld device with a housing and a counter, this objective is attained with the object of claim 11, according to which it is proposed that the counter wheel is realized cylindrically and provided with an engagement toothing, which is preferably realized on a lower peripheral edge during the intended use and acted upon by the drive part in order to realize the rotation of the counter wheel, wherein a remaining outer surface of the counter wheel toward the top can be freely used for applying readable characters, and that the mounting part and the drive part are jointly moved relative to the engagement part, which practically is stationary with respect to the housing and at best slightly moved in the form of a motion transverse to the deflecting motion during an actuation, in order to carry out a counting process.

With respect to the counter for a handheld device, the above-defined objective is furthermore attained with the object of claim 12, according to which it is proposed that the return spring, which is arranged underneath the mounting part referred to an actuating direction, is realized in the form of a bow with two end regions that are fastened on the mounting part, wherein the end regions transform into the mounting part at different locations on the underside thereof, and that the mounting part and the drive part can be jointly moved relative to the engagement part in order to carry out a counting process.

With respect to the handheld device, the mounting part is realized independently of the housing and the drive part is also attached to the mounting part. It is directly attached to the mounting part, i.e. without an intermediate part toward the mounting part. To this end, the drive part may be connected to the mounting part by means of a form-fitting connection such as, e.g., a snap-in mechanism. A very simple design is achieved due to the fact that the drive part is also attached to the mounting part. No additional part is required. The mounting part does not simultaneously form part of the housing of the handheld device. It particularly does not simultaneously form an outer wall of the housing. In fact, the counter with the mounting part is designed for being inserted into a housing of the handheld device.

The return spring, which is arranged underneath the counter referred to the actuating direction thereof and therefore particularly arranged underneath the mounting part and the counter wheel, can have another function, namely a direct interaction with the drive part in order to realize the driving function and thereby the rotation of the counter wheel. In this case, one part can also be advantageously eliminated such that a correspondingly compact design of the counter can be achieved. The engagement part is engaged with the drive part during the course of a deflection of the return spring from an idle position into an actuating position. The engagement part and the drive part preferably do not contact one another in the idle position. During the course of an actuation, the engagement part including an actually engaged engagement end moves relative to the mounting part and the counter wheel, namely in the direction of a central axis of the counter wheel and/or the mounting part.

The cylindrically designed counter wheel may feature the drive part on the outside, i.e. assigned to the surface, on which the readable characters are usually arranged. In this way, the counter wheel is provided with the drive part on one side in a quasi-projecting fashion. Otherwise, the counter wheel may on the other side be directly assigned to a window or a transparent part of the handheld device, in which it should be arranged. A drive part, the rotational axis of which extends outside the counter wheel, can advantageously act upon the counter wheel from outside. In a cylindrical or toroidal or generally curved design of the counter wheel, the convex (outer) side of the counter wheel can be used.

It is furthermore preferred that the engagement part is attached to the mounting part. In this case, the mounting part preferably not only serves for mounting the drive part, but also the engagement part that interacts with the drive part.

The engagement part particularly may be attached to the mounting part by means of a or the aforementioned return spring. The engagement part may be realized integrally with the return spring, particularly in one piece consisting of the same material.

In any case, the mounting part is preferably also realized with an integral mounting formation for the drive part, which consists of the same material.

The mounting part and the drive part can be jointly moved relative to the engagement part, which is stationary with respect to the housing, in order to carry out a counting process. If the engagement part is connected to the return spring as in the preferred embodiment, a certain motion of the return spring transverse to its deflecting motion may in fact occur as a result of the deflecting motion. However, the engagement part is preferably connected to or realized integrally with the region of the return spring, which is also in contact with the housing, particularly a bottom of the housing of the handheld device, in the relaxed state. In that respect, this region practically does not move, at least not vertically or in the deflecting direction of the return spring, but at best slightly in the form of a motion transverse to the deflecting direction during an actuation.

A locking part for acting upon the drive part may furthermore be attached to the mounting part. It is also preferred that the locking part is already realized integrally with the mounting part, particularly in one piece consisting of the same material. Consequently, the mounting part has assumed yet another function and thereby additionally contributes to the realization of a counter with the fewest individual parts possible.

The counter wheel may be realized cylindrically as already mentioned above and feature an engagement toothing, which is preferably realized on a lower peripheral edge during the intended use. Since the engagement toothing is preferably realized on the lower peripheral edge of the preferably cylindrical counter wheel, the remaining (outer) surface (toward the top) can be freely used for applying the readable characters.

The cylindrical design of the counter wheel, in which no additional installation parts are provided in the interior of the thusly formed cylinder body, is also advantageous with respect to the interaction with a receptacle of the handheld device, in which the pharmaceutical substances accommodated. It is preferred that only sections of the mounting part are located in the interior of the counter wheel. The receptacle is typically realized in the form of a so-called canister, which in a longitudinal cross section has a stepped bottom with a central pin-like projection, wherein a tubular valve part, from which the substance is ultimately discharged during an actuation, protrudes from said projection.

The cylindrical design of the counter wheel particularly may be realized in such a way that an upper end face of the cylinder body can be arranged such that it is assigned to the lower, outer step surface of the aforementioned receptacle.

In order to be actuated by a user, the receptacle typically has to be pressed downward against a spring arranged in the receptacle itself such that the motion, which ultimately leads to the actuation of the counter, simultaneously takes place due to the pressure exerted upon the counter wheel or the mounting part accommodating the counter wheel, respectively.

Similarly, the mounting part is preferably realized cylindrically.

It is also preferred that the mounting part overlaps the counter wheel from inside in a longitudinal cross section. Consequently, the outer surface of the counter wheel is exposed. This outer surface preferably carries the aforementioned readable characters.

According to another detail, the drive part may preferably be realized in the form of a worm shaft with toothing projections. This means that a circumferential toothing is in fact provided, but this circumferential toothing on the drive part is realized on a helix that extends obliquely to a rotational axis of the drive part and helically around the rotational axis.

If the counter wheel and/or the mounting part are realized accordingly, the drive part is preferably arranged such that its rotational axis extends transverse to a central axis of the counter wheel and/or the mounting part, which is preferably a cylinder axis.

The engagement part preferably acts upon the drive part on the counter wheel side of the rotational axis of the drive part. Consequently, a very close application point for the force transfer from the driving part to the counter wheel is achieved. The described toothing projections particularly also serve for the interaction between the engagement part and the drive part, as well as the locking part.

The locking part preferably acts upon the drive part on the side of the rotational axis of the drive part, which faces away from the counter wheel. In this way, the drive part initially is acted upon on opposite sides—referred to the rotational axis of the locking part and the drive part. The aforementioned parts can simultaneously move toward one another without any risk of obstruction.

The locking part and the engagement part are preferably arranged such that they are directed oppositely. The free ends of the locking part and the engagement part are arranged such that they are directed toward one another. In this case, the locking part particularly may be arranged on the upper side and the engagement part may be arranged on the lower side—referred to the described installation state, in which the counter is acted upon by the receptacle from above.

The engagement part and/or the locking part are arranged outside the counter wheel or the mounting part in general—referred to a view from above or below, in which a central axis of the counter wheel and/or the mounting part forms a point. In other respects, the arrangement outside the mounting part refers to the fact that the connection for the engagement part, which—with reference to one embodiment—is realized by the return spring itself, or the connection for the locking part, which then insofar also form parts of the mounting part, already are considered as lying outside the mounting part to the extent, to which they are visible in the aforementioned view.

In the aforementioned view, the return spring may also laterally extend beyond the engagement part and/or the locking part.

The return spring itself is preferably realized in the form of a bow, particularly a closed bow. The bow has two ends that are fastened on the mounting part. The fastening regions, for example in the form of connecting points, may lie approximately opposite of one another referred to a diameter line of the preferably cylindrical mounting part and the cylinder defined by the mounting walls. They may also lie opposite of one another on a secant referred to a thusly formed circle of the cylinder. In the latter instance, the fastening regions or the connecting points are preferably arranged offset to the central axis in such a way that the central axis lies between the secant and the locking part and/or the engagement part, wherein this once again refers, for example, to the view from above, in which the central axis forms a point.

The counter wheel is preferably realized in the form of an integral cylinder part.

The invention is described in greater detail below with reference to the attached drawings that, however, merely show an exemplary embodiment. In these drawings:

FIG. 6 shows a cross section through the counter wheel attached to the mounting part;

FIG. 7 shows a schematic top view of the housing of the handheld device in the direction of the bottom of the housing while the counter is removed, namely in the version, in which the engagement part is integrally formed on the housing; and FIG. 8 shows an illustration according to FIG. 7 in the version, in which the engagement part is integrally formed on the return spring.

A counter 1 consisting of a counter wheel 2, a mounting part 3 and a drive part 4 is described and illustrated below; see particularly FIGS. 4, 5.

These few parts, preferably only three parts, are essential to this counter wheel. It is particularly important that the mounting part is realized integrally with additional functions and functional parts, preferably in one piece consisting of the same material.

Figure 1:
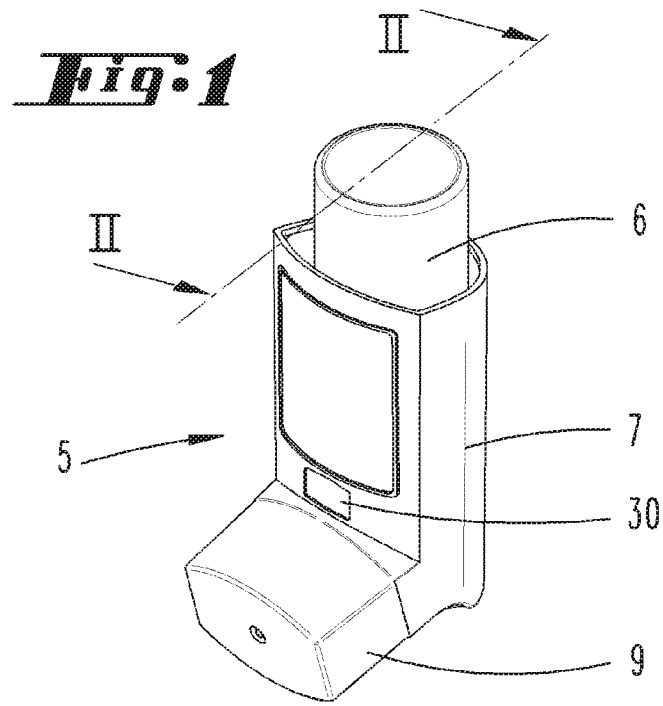
FIG. 1 shows a perspective exterior view of an exemplary handheld device with a receptacle arranged therein and an (invisible) counter.

The counter 1 can be arranged in a handheld device 5 of the type illustrated in principle in FIG. 1.

Figure 2:
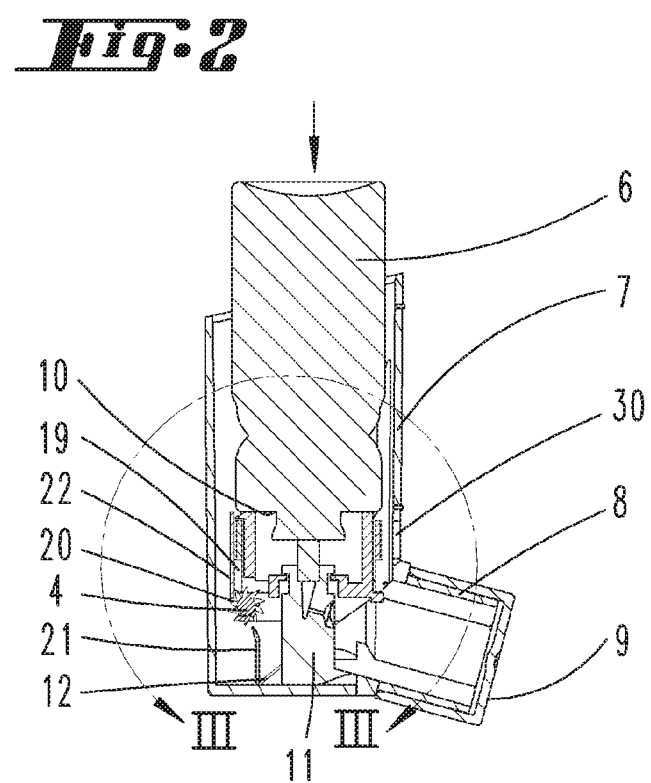
FIG. 2 shows a cross section through the object of FIG. 1 along the plane II-II. This figure schematically shows the arrangement of the counter in the housing of the handheld device.

The cross section according to FIG. 2 furthermore shows that a receptacle 6 containing the pharmaceutical substance to be dispensed can be arranged in the handheld device 5. The handheld device 5 particularly consists of an inhalation device.

The handheld device 5 furthermore features a housing 7 that comprises a section, which extends vertically during the intended use and in which a receptacle 6 is accommodated, as well as a mouthpiece 8 that angularly protrudes from this vertical section, e.g. at a right angle or obtuse angle referred to a longitudinal axis of the vertical section. The mouthpiece 8 may be covered with a cap 9 when the handheld device is not in use.

The entire counter 1 is accommodated in the housing 7 of the handheld device 5.

According to FIG. 2, the counter 1 particularly may be arranged underneath the receptacle 6, the lower side of which is realized in a stepped fashion in a longitudinal cross section, particularly such that the mounting part 3 can come in direct contact with a step surface, preferably an outer step surface 10 of the receptacle 6. The receptacle 6 is actuated by being pressed downward against a not-shown spring that is arranged in the receptacle itself, namely relative to a stationary receiving and dispensing stub 11 in the housing 7.

In this case, the mounting part 3 and the counter wheel 2 accordingly are jointly pressed downward against a return spring 12 that is preferably realized on the mounting part. While the mounting part and the counter wheel are pressed downward, the drive part 4 interacts with the counter wheel 1 in order to rotationally drive this counter wheel 1 about a central axis A thereof, which may also be a cylinder axis as discussed further below.

The described counter 1 particularly is not designed for individually counting each actuation of the handheld device 5. However, it may also be realized in the form of an individual counter. The counter preferably only displays a new numeral (completely) after a certain number of actuations, for example after 5, 10 or 20 respective actuations.

The counter wheel 2 apparently features corresponding readable characters 13, particularly on an outer circumferential surface of the preferably cylindrical counter wheel 2.

The characters 13 can be read through a window 30 in the housing 7.

The counter wheel 2 is mounted on the mounting part 3. To this end, the mounting part 3 engages behind the counter wheel 2 with mounting fingers 14 and/or a mounting wall 15 as illustrated in greater detail, e.g., in FIG. 6. The mounting fingers 14 may be realized such that they can be elastically deflected. Due to a lead-in chamfer 16 on the mounting finger 14, the counter wheel 2 can be mounted on the mounting part 3 by simply being coaxially pushed on the mounting part 3 from above. The mounting fingers 14 can yield inward and, once the counter wheel 2 is completely attached, overlap the counter wheel 2 with an upper overlapping formation due to their elastic restoration as shown in FIG. 4. The lower side of the counter wheel 2 may be seated on a step surface 17 of the mounting part 3. The mounting part 3 preferably also features a bottom 26. Furthermore, the bottom 26 preferably features a mounting opening 27, by means of which the counter 1 may be snap-mounted on the receiving/dispensing stub 11 of the housing 7 in the installed state; see FIG. 2.

Furthermore, the bottom 26 is preferably realized approximately at the height of the step surface 17. The bottom is preferably also realized such that it only extends on the inner side of the mounting wall and essentially perpendicular to the central axis A.

Snap-in fingers may also be realized in the mounting opening 27 in order to promote the potential mounting of the counter on the receiving/dispensing stub 11 of the housing of the device.

To this end, the mounting stub 11 apparently features a circumferential groove 29, into which such snap-in fingers can engage. In the illustration in FIG. 3, the bottom 26 and, in particular, the aforementioned snap-in fingers are in an upper position referred to the groove 29 because this figure shows the relaxed position and the counter 3 is pressed into the upper position by the return spring 12. During the course of an actuation, the bottom and the counter 1 can altogether move relative to the housing and, in particular, relative to the receiving/dispensing stub 11 by the vertical height (width) of the groove 29.

The lower side of the counter wheel 2 is realized with an engagement toothing 18. This engagement tooting makes it possible to act upon the counter 1 in order to realize its rotation.

The engagement toothing 18 is acted upon by the drive part 4.

The mounting part 3 is preferably also realized toroidal, particularly cylindrical, if applicable with different regions in a vertical direction of a cylinder axis, which preferably coincides with the central axis A. A functional section is preferably provided underneath the step surface. This functional section, which preferably also as an annular shape, particularly a cylindrical shape, is provided with one or more formations that can fulfill one or more functions. A mounting formation 25 is initially provided for mounting the drive part 4. It may consist of snap-in openings for an axis of the drive part 4. Rib-like counter formations 24 for the mounting in a housing of the handheld device are furthermore provided. In addition, the functional section features the connection of the return spring 12. This return spring may extend from a lower end face of the functional section. Referred to the side view according to FIG. 2, in which the central axis A forms a line and the rotational axis D forms a point, the direction of extent of said return spring preferably includes an acute angle with the central axis A. The return spring 12 is preferably designed in a bow-like fashion, particularly such that the two bow arms of the bow overlap in the aforementioned side view and only the bow arm is visible.

It is furthermore preferred that the return spring 12 has a closed bow-like design. In other respects (i.e. with consideration of these purposes without the return spring 12), two end regions of the bow are preferably realized such that they transform into the mounting part 3 at two different locations on the underside thereof.

According to another detail, the drive part 4 is realized in the form of a worm shaft, preferably a single-flight worm shaft. This is also illustrated, e.g., in FIG. 6. A helical pitch may be adapted to the spacing between two adjacent toothing projections 19 of the counter wheel 2. The actual counting effect referred to one respective actuation can be adjusted due to this measure and due to the fact that the counter wheel is driven by a defined amount of a toothing projection 19 during one revolution.

One respective driving projection 20, which may simultaneously also serve as a tooth for acting upon the engagement part 21, particularly can engage between two driving projections 20 and drive the counter wheel 2 during a rotation due to the helical or screw-like design.

The engagement part 21 is preferably realized on the return spring 12 and particularly consists of the same material as the return spring 12.

Figure 5:
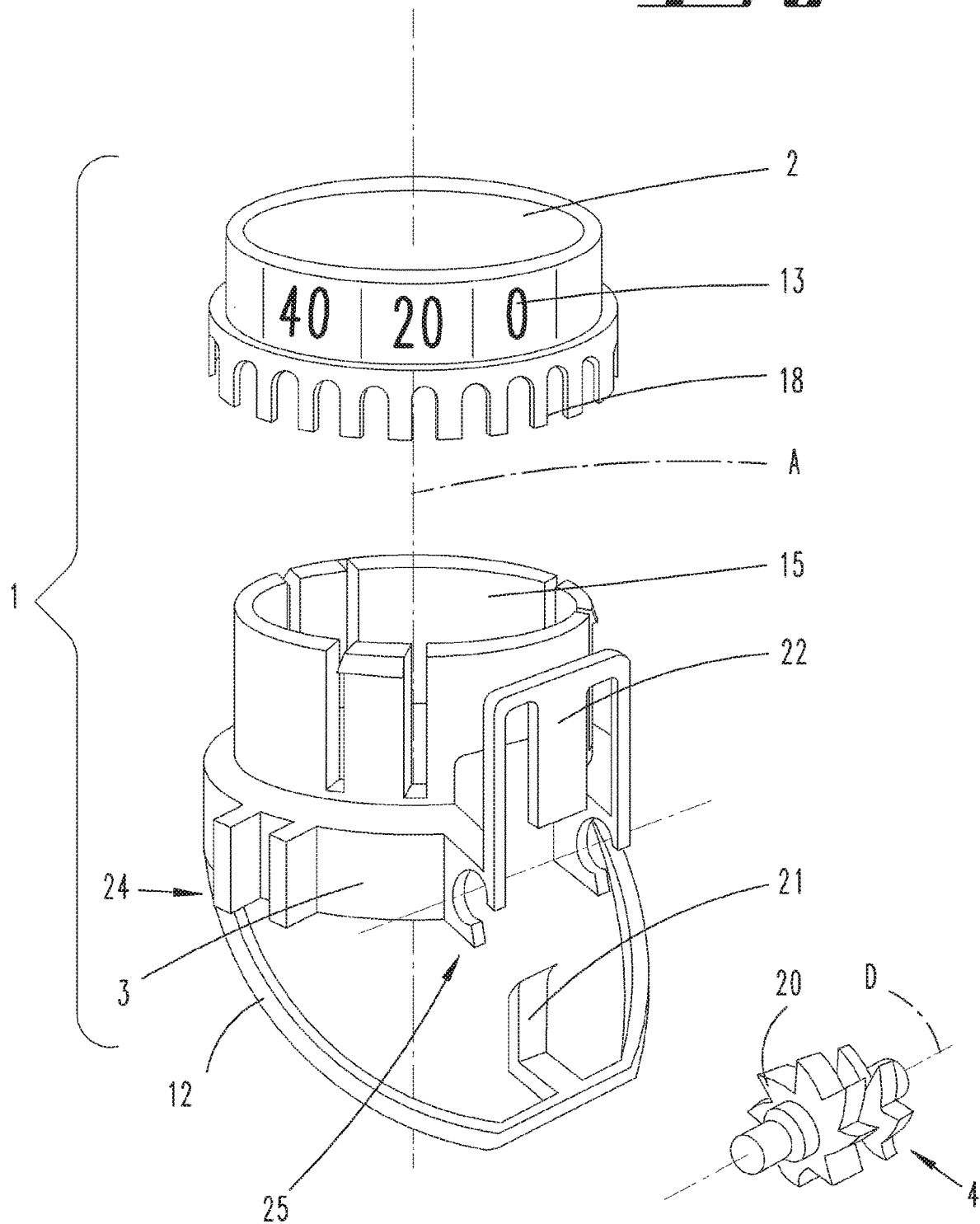
FIG. 5 shows an exploded view according to FIG. 4, in which the engagement part is integrally formed on the return spring.

According to FIG. 5, for example, the engagement part 21 may be arranged on a region of the return spring, which projects farthest transverse to the rotational axis D, but preferably once again extends back in the direction of the central axis A.

Figure 4:
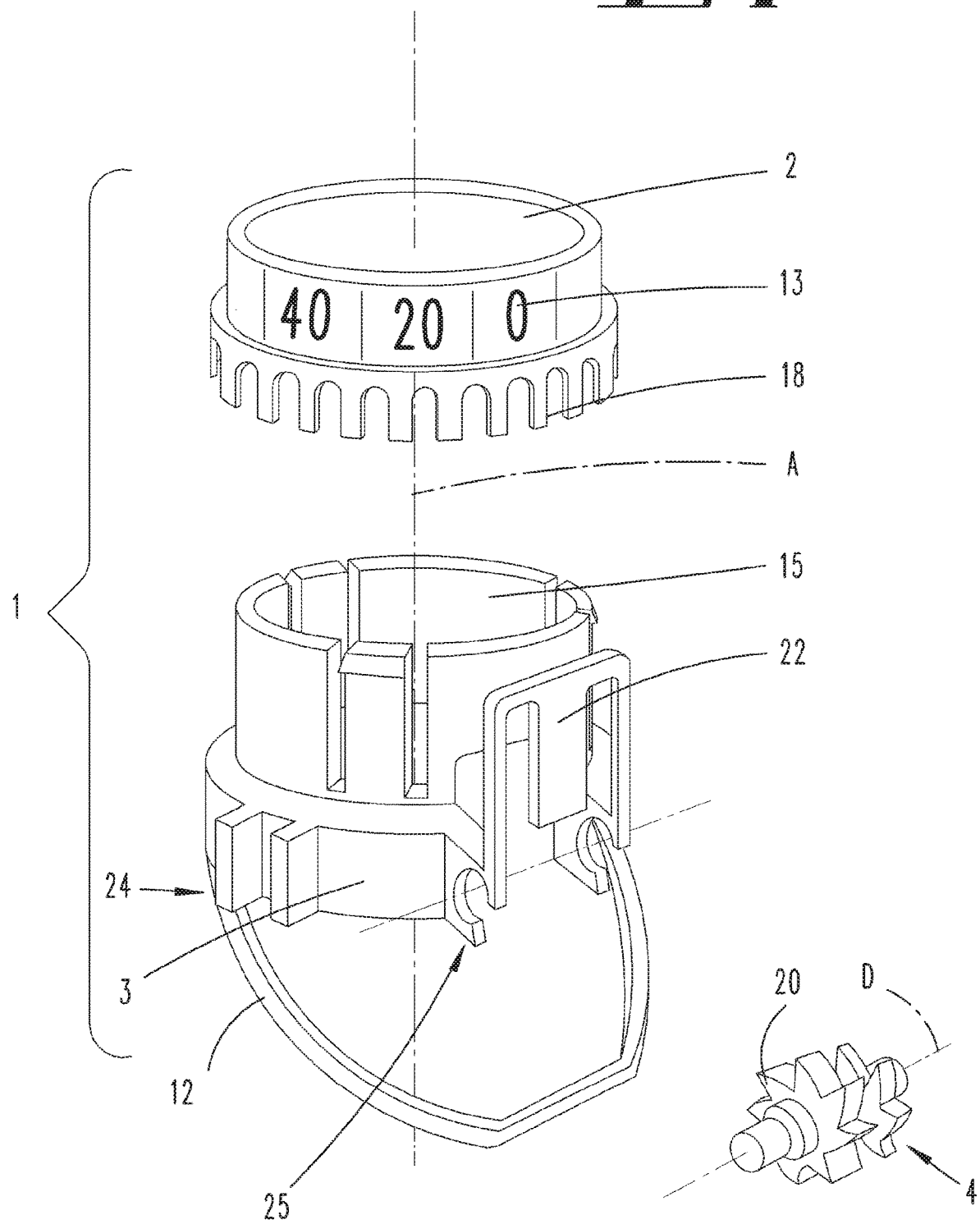
FIG. 4 shows an exploded view of the counter in the version, in which the engagement part is integrally formed on the housing.

The engagement part 21 may alternatively also be directly arranged on the housing 7 as illustrated in FIG. 7 and in FIG. 4, in which it is not integrally formed on the return spring 12. It may be mounted thereon in a plug-type fashion. Furthermore, it may preferably be realized integrally with the housing 7 in one piece consisting of the same material.

According to FIGS. 5 and 7, for example, the engagement part 21 is preferably also designed similar to a blade that extends straight such that only the narrow rectangular outline is visible in FIG. 7. A certain curved or bent formation may also be provided on the free end on the upper side of the engagement part 21 as illustrated in the embodiment according to FIG. 2 and FIG. 3.

During an actuation of the handheld device, i.e. when the receptacle is pressed downward in the exemplary embodiment, the engagement projection 21 remains approximately stationary relative to the housing 7. If the engagement projection is integrally formed on or connected to the return spring 12, it may move slightly transverse to the central axis A as a result of the deflecting motion of the spring.

During an actuation of the handheld device, the engagement projection 21 encounters a driving projection 20 of the drive part 4 and causes a rotation of the worm shaft about the rotational axis D of the drive part 4.

A backward rotation of the drive part 4 is simultaneously prevented by means of a locking part 22. The locking part 22 also interacts with the worm shaft, particularly with the toothing projections 19 of the drive part 4 that form the helical design.

Figure 3:
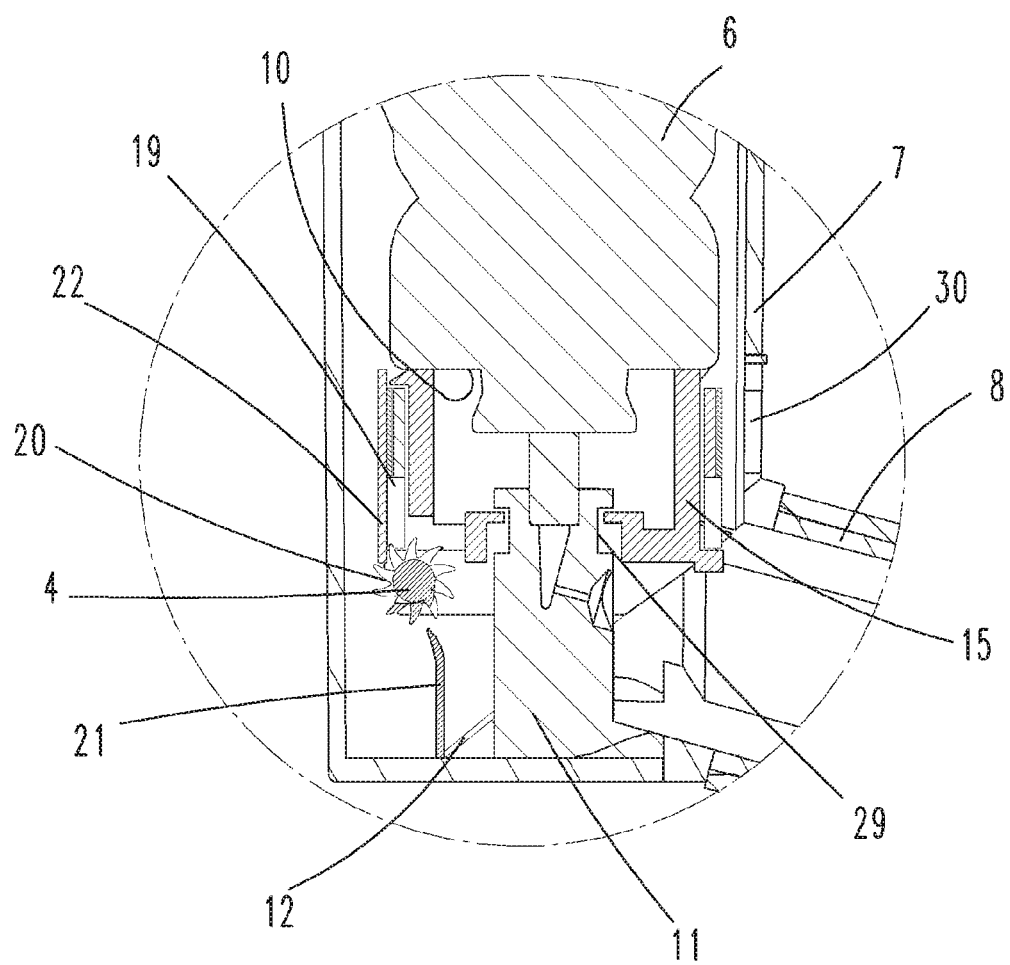
FIG. 3 shows an enlarged detail of the region III-III in FIG. 2.

The drive part 4 interacts with the locking part 22 on the opposite side of the corresponding interaction of the drive part 4 with the engagement part 21—referred to a side view according to FIG. 2 or FIG. 3, in which the rotational axis D of the drive part forms a point.

The locking part 22 and the engagement part 21 are preferably directed oppositely. They may respectively consist of flat parts that extend in the direction of the central axis A and approximately parallel thereto. The engagement part 21 and/or the locking part 22 may also feature a hook-shaped formation on the upper side on the respective free end in order to promote the interaction with a driving projection 20.

According to FIG. 7, the housing 7 of the handheld device features circumferentially distributed rib formations 23 on its inner side. These rib formations 23 serve for securing the counter 1 against rotating. To this end, they may interact with the counter formations 24 on the mounting part 3. They may furthermore form a restricted guidance for the return spring 12.

The preceding explanations serve for elucidating all inventions that are included in this application and respectively enhance the prior art independently with at least the following combinations of characteristics, namely:

A counter, which is characterized in that the mounting part is realized independently of the housing 7, and in that the drive part 4 is directly attached to the mounting part 3.

A counter, which is characterized in that the counter 1 features a return spring 12 for the retrodisplacement after an actuation, and in that the spring 12, which is realized separately of the drive part 4, features an engagement part 21 for interacting with the drive part 4.

A counter, which is characterized in that the rotational axis D extends outside the counter wheel 2, namely also with respect to a projection of the counter wheel 2 in the direction of the central axis A of the counter wheel 2.

A counter, which is characterized in that the engagement part 21 is attached to the mounting part 3.

A counter, which is characterized in that the engagement part 21 is attached to the mounting part 3 by means of a return spring 12.

A counter, which is characterized in that the mounting part 3 and the drive part 4 are jointly moved relative to the engagement part 21, which is stationary with respect to the housing 7, in order to carry out a counting process.

A counter, which is characterized in that a locking part 22 for acting upon the drive part 4 is attached to the mounting part 3.

A counter, which is characterized in that the counter wheel is realized cylindrically and/or with an engagement toothing 18, which is formed on a lower peripheral edge during the intended use.

A counter, which is characterized in that the drive part 4 has a rotational axis D, and in that the rotational axis D extends transverse to a central axis A of the counter wheel 2.

A counter, which is characterized in that the engagement part 21 acts upon the drive part 4 on the counter wheel side of the rotational axis D.

A counter, which is characterized in that the locking part 22 acts upon the drive part 4 on the side of the rotational axis D of the drive part 4, which faces away from the counter wheel 2.

A counter, which is characterized in that the locking part 22 and the engagement part 21 are arranged such that they are directed oppositely.

LIST OF REFERENCE SYMBOLS

1 Counter
2 Counter wheel
3 Mounting part
4 Drive part
5 Handheld device
6 Receptacle
7 Housing
8 Mouthpiece
9 Cap
10 Step surface
11 Receiving/dispensing stub
12 Return spring
13 Character
14 Mounting finger
15 Mounting wall
16 Lead-in chamfer
17 Step surface
18 Engagement toothing
19 Toothing projection
20 Driving projection
21 Engagement part
22 Locking part
23 Rib formation
24 Counter formation
25 Mounting projection
26 Bottom
27 Mounting opening
28 Overlapping formation
29 Groove
30 Window
A Central axis
D Rotational axis

The invention claimed is:

1. A handheld device (5) for dispensing a pharmaceutical substance with a housing (7) and a counter (1), wherein the counter (1) features at least one counter wheel (2) with readable characters (13) and a drive part (4) with a rotational axis (D) designed for rotating the counter wheel (2), wherein the counter wheel (2) is rotatably attached to a mounting part (3), wherein the mounting part (3) is formed independently of the housing (7), and wherein the drive part (4) is directly attached to the mounting part (3), wherein the counter wheel (2) is formed as a hollow cylinder and s provided with an engagement toothing (18), which is formed on a lower peripheral edge during the intended use and acted upon by the drive part (4) in order to achieve the rotation of the counter wheel (2), wherein a remaining outer surface of the counter wheel (2) toward the top can be freely used for applying readable characters, and wherein the mounting part (3) and the drive part (4) are jointly moved relative to an engagement part (21), which is stationary with respect to the housing (7), in order to carry out a counting process, wherein the mounting part (3) engages the counter wheel from within the interior of the counter wheel (2) via elastically deflectable mounting fingers (14) that are configured to overlap the counter wheel (2) with an upper overlapping formation upon engagement of the mounting part with the counter wheel (2), wherein a lower side of the counter wheel (2) is seated outside on a step surface (17) of the mounting part, wherein the mounting part has snap-in openings for receiving an axis of the drive part and a connection for a return spring (12) which extends from a lower end of a functional section of the mounting part, and wherein the drive part is in the form of a worm shaft with a helical pitch that engages with the teeth (18).

2. The handheld device according to claim 1, wherein the rotational axis (D) of the drive part extends outside the counter wheel, namely also with respect to a projection of the counter wheel (2) in the direction of a central axis (A) of the counter wheel (2).

3. The handheld device according to claim 1, wherein the engagement part (21) is attached to the mounting part (3) by means of a return spring (12).

4. The handheld device according to claim 1, further comprising a locking part (22) configured for acting upon the drive part (4), the locking part being attached to the mounting part (3).

5. The handheld device according to claim 4, wherein the locking part (22) and the engagement part (21) are arranged such that they are directed oppositely.

6. The handheld device according to claim 1, wherein the rotational axis (D) extends transverse to a central axis (A) of the counter wheel (2).

7. The handheld device according to claim 1, wherein the engagement part (21) acts upon the drive part (4) on the counter wheel side of the rotational axis (D).

8. The handheld device according to claim 1, further comprising a locking part (22) that acts upon the drive part (4) on the side of the rotational axis (D) of the drive part (4), which faces away from the counter wheel (2).

9. The handheld device according to claim 1, wherein the helical pitch of the drive part (4) has toothing projections that form a circumferential toothing with a helix, which extends obliquely to a rotational axis (D) of the drive part (4) and helically around the rotational axis (D).

10. A counter (1) for a handheld device (5) for dispensing a pharmaceutical substance with at least one counter wheel (2) formed as a hollow cylinder with readable characters (13) and a drive part (4) with a rotational axis (D) designed for rotating the counter wheel (2), wherein the counter (1) features a return spring (12), which is formed separately from the drive part, for the retrodisplacement after an actuation, wherein the spring (12), features an engagement part (21) for interacting with the drive part (4), and wherein the counter wheel (2) is furthermore rotatably attached to the mounting part (3), wherein the return spring (12), which is arranged underneath the mounting part (3) in reference to an actuating direction, is in the form of a bow with two end regions that are fastened on the mounting part (3), wherein the end regions transition into the mounting part (3) at different locations on the underside thereof, wherein the mounting part (3) and the drive part (4) can be jointly moved relative to the engagement part (21) in order to carry out a counting process, wherein the mounting part (3) engages the counter wheel from within the interior of the counter wheel (2) via elastically deflectable mounting fingers (14) that are configured to overlap the counter wheel (2) with an upper overlapping formation upon engagement of the mounting part with the counter wheel (2), wherein a lower side of the counter wheel (2) is seated outside on a step surface (17) of the mounting part, wherein the mounting part has snap-in openings for receiving an axis of the drive part and a connection for a return spring (12) which extends from a lower end of a functional section of the mounting part, and wherein the drive part is in the form of a worm shaft with a helical pitch that engages with the teeth (18).

11. The counter according to claim 10, wherein the rotational axis (D) extends outside the counter wheel (2), namely also with respect to a projection of the counter wheel (2) in the direction of a central axis (A) of the counter wheel (2).

12. The counter according to claim 10, wherein the engagement part (21) is attached to the mounting part (3) by means of a return spring (12).

13. The counter according to claim 10, further comprising a locking part (22) configured for acting upon the drive part (4), the locking part being attached to the mounting part (3).

14. The counter according to claim 13, wherein the locking part (22) and the engagement part (21) are arranged such that they are directed oppositely.

15. The counter according to claim 10, wherein the rotational axis (D) extends transverse to a central axis (A) of the counter wheel (2).

16. The counter according to claim 10, wherein the engagement part (21) acts upon the drive part (4) on the counter wheel side of the rotational axis (D).

17. The counter according to claim 10, further comprising a locking part (22) that acts upon the drive part (4) on the side of the rotational axis (D) of the drive part (4), which faces away from the counter wheel (2).

18. The counter according to claim 10, wherein the helical pitch of the drive part (4) has toothing projections that form a circumferential toothing with a helix, which extends obliquely to a rotational axis (D) of the drive part (4) and helically around the rotational axis (D).

* * * * *